US010539675B2

(12) United States Patent
Zalev

(10) Patent No.: US 10,539,675 B2
(45) Date of Patent: Jan. 21, 2020

(54) OPTO-ACOUSTIC IMAGING SYSTEM WITH DETECTION OF RELATIVE ORIENTATION OF LIGHT SOURCE AND ACOUSTIC RECEIVER USING ACOUSTIC WAVES

(71) Applicant: Seno Medical Instruments, Inc., San Antonio, TX (US)

(72) Inventor: Jason Zalev, Thornhill (CA)

(73) Assignee: Seno Medical Instruments, Inc., San Antonio, TX (US)

( * ) Notice: Subject to any disclaimer, the term of this patent is extended or adjusted under 35 U.S.C. 154(b) by 1102 days.

(21) Appl. No.: 14/928,201

(22) Filed: Oct. 30, 2015

(65) Prior Publication Data

US 2016/0187481 A1 Jun. 30, 2016

Related U.S. Application Data

(60) Provisional application No. 62/072,997, filed on Oct. 30, 2014.

(51) Int. Cl.
*G01S 15/89* (2006.01)
*G01S 15/06* (2006.01)
(Continued)

(52) U.S. Cl.
CPC ........ *G01S 15/8965* (2013.01); *A61B 5/0095* (2013.01); *A61B 34/20* (2016.02);
(Continued)

(58) Field of Classification Search
CPC ....... A61B 34/20; A61B 5/0095; A61B 90/37; A61B 2034/2055; A61B 2034/2057;
(Continued)

(56) References Cited

U.S. PATENT DOCUMENTS

| 4,267,732 A | 5/1981 | Quate |
| 5,394,875 A | 3/1995 | Lewis et al. |

(Continued)

FOREIGN PATENT DOCUMENTS

| EP | 0282234 A1 | 9/1988 |
| EP | 1953564 A2 | 8/2008 |

(Continued)

OTHER PUBLICATIONS

Chepuri, Sundeep Prabhakar, "Rigid Body Localization Using Sensor Networks", IEEE Transactinos on Signal Processing, vol. 62, No. 18, Sep. 15, 2014 pp. 4911-4924.
(Continued)

*Primary Examiner* — Baisakhi Roy
(74) *Attorney, Agent, or Firm* — Dean D. Small; The Small Patent Law Group, LLC

(57) ABSTRACT

In an embodiment, a system and method are provided for determining position and orientation of an optical delivery unit relative to an acoustic receiving unit, in the field of opto-acoustic imaging, wherein the optical delivery unit comprises a first fiducial marker site configured to emit acoustic responses and a second fiducial marker site configured to emit acoustic responses. A plurality of acoustic signals from a volume of a subject are sampled and recorded, each of the plurality of acoustic signals being collected at a different data collection position relative to a coordinate reference frame. The system is configured to identify in each of the plurality of acoustic signals a response of a first fiducial marker and a response of a second fiducial marker. Each identified response indicates a separation between a fiducial marker site and a data collection position of an acoustic signal. The system determines the position and orientation of the optical delivery unit in the coordinate reference frame by using the identified responses of the first
(Continued)

fiducial marker and the identified responses of the second fiducial marker.

25 Claims, 6 Drawing Sheets

(51) Int. Cl.
    *A61B 34/20* (2016.01)
    *A61B 5/00* (2006.01)
    *A61B 90/00* (2016.01)
(52) U.S. Cl.
    CPC .............. *A61B 90/37* (2016.02); *G01S 15/06* (2013.01); *A61B 2034/2055* (2016.02); *A61B 2034/2057* (2016.02)
(58) Field of Classification Search
    CPC ......... A61B 5/064; A61B 8/0841; A61B 8/15; G01S 15/06
    USPC ........................................................ 600/424
    See application file for complete search history.

(56) References Cited

U.S. PATENT DOCUMENTS

| | | | |
|---|---|---|---|
| 5,504,281 A | 4/1996 | Whitney et al. | |
| 5,713,356 A | 2/1998 | Kruger | |
| 5,840,023 A | 11/1998 | Oraevsky et al. | |
| 5,977,538 A | 11/1999 | Unger et al. | |
| 6,167,295 A * | 12/2000 | Cosman ................. | A61B 90/10 600/414 |
| 6,263,094 B1 | 7/2001 | Rosich et al. | |
| 6,275,725 B1 * | 8/2001 | Cosman ................. | G06K 9/28 600/426 |
| 6,751,490 B2 | 6/2004 | Esenaliev et al. | |
| 7,735,349 B2 | 6/2010 | Hochmitz | |
| 7,972,272 B2 | 7/2011 | Munce et al. | |
| 8,016,419 B2 | 9/2011 | Zhang et al. | |
| 8,025,406 B2 | 9/2011 | Zhang et al. | |
| 8,144,327 B2 | 3/2012 | Nakajima et al. | |
| 8,214,010 B2 | 7/2012 | Courtney et al. | |
| 8,298,144 B2 | 10/2012 | Burcher | |
| 8,300,224 B2 | 10/2012 | Nakajima et al. | |
| 8,353,830 B2 | 1/2013 | Kanayama et al. | |
| 8,353,833 B2 | 1/2013 | Dogra et al. | |
| 8,460,195 B2 | 6/2013 | Courtney et al. | |
| 8,480,584 B2 | 7/2013 | Kanayama et al. | |
| 8,712,506 B2 | 4/2014 | Courtney et al. | |
| 8,784,321 B2 | 7/2014 | Courtney et al. | |
| 8,870,770 B2 | 10/2014 | Dogra et al. | |
| 8,876,717 B2 | 11/2014 | Tokita et al. | |
| 9,330,452 B2 | 5/2016 | Zalev et al. | |
| 9,357,923 B2 | 6/2016 | Courtney et al. | |
| 9,375,147 B2 | 6/2016 | Courtney et al. | |
| 9,700,214 B2 | 7/2017 | Ichihara et al. | |
| 2001/0022657 A1 | 9/2001 | Autrey et al. | |
| 2005/0004458 A1 | 1/2005 | Kanayama et al. | |
| 2007/0093698 A1 * | 4/2007 | Goldberger ......... | A61B 5/0095 600/310 |
| 2008/0071172 A1 | 3/2008 | Bruck et al. | |
| 2008/0177183 A1 | 7/2008 | Courtney et al. | |
| 2009/0247903 A1 | 10/2009 | Rivet et al. | |
| 2010/0049044 A1 | 2/2010 | Burcher | |
| 2010/0094134 A1 | 4/2010 | Zhu et al. | |
| 2010/0168568 A1 * | 7/2010 | Sliwa ........................ | A61B 8/12 600/439 |
| 2010/0249562 A1 | 9/2010 | Zhang et al. | |
| 2010/0249570 A1 | 9/2010 | Carson et al. | |
| 2010/0298688 A1 | 11/2010 | Dogra et al. | |
| 2011/0054292 A1 | 3/2011 | Hirson et al. | |
| 2011/0201914 A1 | 8/2011 | Wang et al. | |
| 2011/0303015 A1 | 12/2011 | Ichihara et al. | |
| 2011/0306857 A1 | 12/2011 | Razansky et al. | |
| 2011/0319743 A1 | 12/2011 | Satoh | |
| 2012/0165677 A1 | 6/2012 | Li et al. | |
| 2012/0232364 A1 | 9/2012 | Delmage | |
| 2013/0041267 A1 | 2/2013 | Ntziachristos et al. | |
| 2013/0184571 A1 | 7/2013 | Wilkening et al. | |
| 2013/0190591 A1 | 7/2013 | Hirson et al. | |
| 2013/0190595 A1 * | 7/2013 | Oraevsky .............. | A61B 5/0095 600/407 |
| 2013/0335441 A1 | 12/2013 | Zalev et al. | |
| 2014/0007690 A1 | 1/2014 | Hirota | |
| 2014/0051969 A1 | 2/2014 | Suzuki | |
| 2014/0187902 A1 | 7/2014 | Sato et al. | |
| 2014/0198606 A1 | 7/2014 | Morscher et al. | |
| 2014/0221810 A1 | 8/2014 | Kacprowicz | |
| 2014/0303476 A1 | 10/2014 | Dogra et al. | |
| 2014/0323860 A1 | 10/2014 | Courtney et al. | |
| 2015/0031990 A1 * | 1/2015 | Boctor ................... | A61B 8/483 600/424 |
| 2015/0101411 A1 | 4/2015 | Zalev et al. | |
| 2015/0223903 A1 * | 8/2015 | Bell ....................... | A61B 5/0095 600/424 |
| 2015/0300816 A1 * | 10/2015 | Yang ...................... | A61B 90/35 600/424 |
| 2016/0249812 A1 | 9/2016 | Wang et al. | |
| 2016/0302763 A1 | 10/2016 | Courtney et al. | |
| 2017/0112474 A1 | 4/2017 | Burcher | |

FOREIGN PATENT DOCUMENTS

| | | |
|---|---|---|
| JP | 2014144109 A | 8/2014 |
| WO | 2013/056089 A2 | 4/2013 |
| WO | 2013112626 A1 | 8/2013 |
| WO | 2014/050020 A1 | 4/2014 |

OTHER PUBLICATIONS

Hamilton, James D., et al. "High frequency optoacoustic arrays using etalon detection." IEEE transactions on ultrasonics, ferroelectrics, and frequency control 47.1 (2000): 160-169.

Ermilov, Sergey A., et al. "Laser optoacoustic imaging system for detection of breast cancer." Journal of biomedical optics 14.2 (2009): 024007-024007.

Ali, Murtaza, Dave Magee, and Udayan Dasgupta. "Signal processing overview of ultrasound systems for medical imaging." SPRAB12, Texas Instruments, Texas (2008).

* cited by examiner

OPTO-ACOUSTIC IMAGING SYSTEM WITH DETECTION OF RELATIVE ORIENTATION OF LIGHT SOURCE AND ACOUSTIC RECEIVER USING ACOUSTIC WAVES

This application is a non-provisional of and claims priority to U.S. Patent Application No. 62/072,997 filed Oct. 30, 2014, the entire disclosure of which is incorporated herein by reference. This provisional application relates to opto-acoustic imaging systems such as those described in U.S. patent application Ser. No. 13/793,808 filed 11 Mar. 2013, the entire disclosure of which is incorporated herein by reference.

FIELD

The present invention relates in general to the field of medical imaging, and in particular to opto-acoustic imaging systems.

BRIEF DESCRIPTION OF THE DRAWINGS

Objects, features, and advantages of the invention will be apparent from the following detailed description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1A:
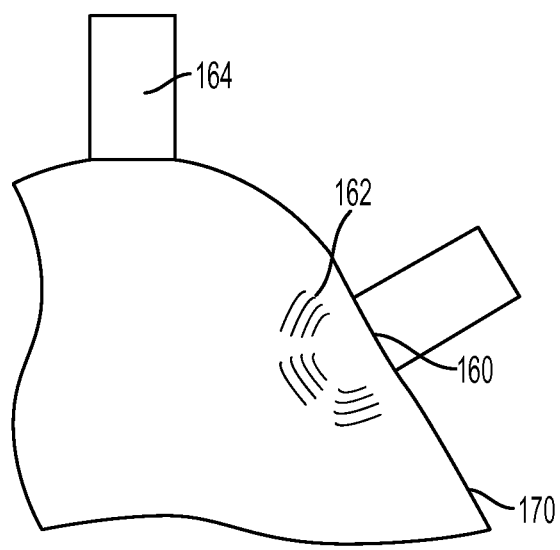
FIGS. 1a and 1b are diagrams showing acoustic waves traveling through a tissue volume from an acoustic source to a proximate object.

Reference will now be made in detail to the preferred embodiments of the present invention, examples of which are illustrated in the accompanying drawings. The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "an embodiment" or "the embodiment" means that a particular feature, structure, or characteristic described in connection with the embodiment is included in at least an embodiment of the disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The present invention is described below with reference to block diagrams and operational illustrations of methods and devices for performing opto-acoustic imaging. It is understood that each block of the block diagrams or operational illustrations, and combinations of blocks in the block diagrams or operational illustrations, may be implemented by means of analog or digital hardware and computer program instructions. These computer program instructions may be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

When a handheld acoustic receiver and handheld light source are manually positioned proximate to tissue, the relative orientation and relative position of the light source is unknown. For opto-acoustic image formation using signals from the acoustic receiver, this presents a challenge, as knowing light source position and orientation are important for this process. Furthermore, the surface of the volume of tissue is subject to unknown deformation, and loss of or partial contact with the source or receiver.

A solution is to track the relative orientation and/or position of the light source with respect to the probe. In an ideal situation, locating inertial positioning devices on both the acoustic receiver and on the light source would track the position and orientation of each device, and thus the relative positions and orientations could be computed from this information coupled with known initial reference positions. However, inertial positioning devices are subject to reliability issues. A reliable method, that might or might not be coupled with an inertial positioning implementation, involves using acoustic waves.

Figure 1B:
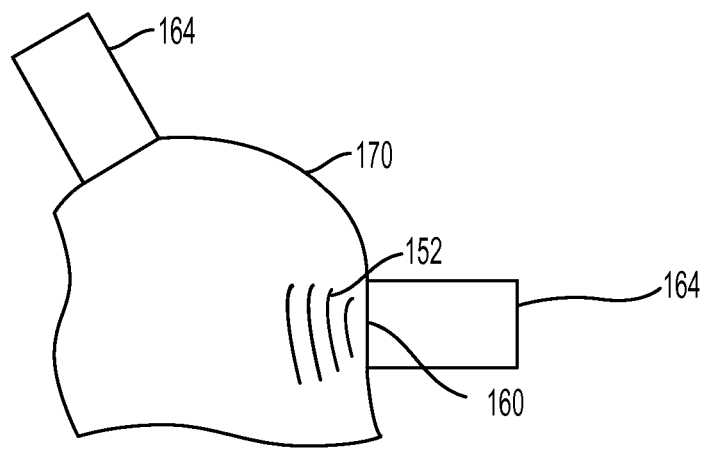

FIGS. 1a and 1b are diagrams showing acoustic waves traveling through a tissue volume 170 from an acoustic source 160 to one or more proximate objects 164. Acoustic waves travel through the tissue volume 170 from one point on the tissue surface to another point on the surface. Acoustic waves may travel from an acoustic source 160 proximate to the surface of the tissue to reach a proximate object 164, proximate to the surface of the tissue. In such a manner, the propagation time, and/or directional information from the wave may be used to compute the position and orientation of the acoustic source relative to the proximate object (see FIG. 1). In an embodiment, an acoustic transmitter, such as a transducer array, may transmit one or multiple directed acoustic wavefronts 162, each wavefront directed towards a particular direction. In an embodiment, the acoustic transmitter may transmit a non-directional wavefront. In an embodiment, the transmitter is located on the acoustic receiver. In an embodiment, the transmitter is located on the light source. In an embodiment, the transmitted wavefront may be received by a detector on an object 164 proximate to the tissue, such as on the light source or on the acoustic receiver. In an embodiment, the detector may be the receiving elements of the acoustic receiver. In an embodiment, the detector may be located on the light source. In an embodiment, the transmitted acoustic wavefront is directly received by the acoustic detector on the proximate object. In an embodiment, the transmitted acoustic wavefront backscatters off of the proximate object 164. In an embodiment, the transmitted acoustic wavefront is transmitted by the same receiving elements as used by the acoustic receiver.

Figure 2:
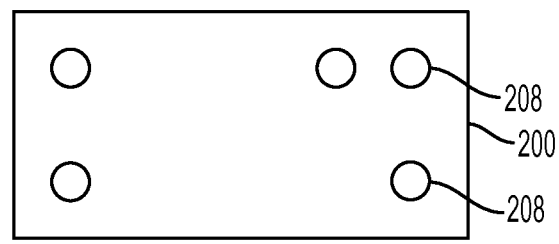
FIG. 2 is a diagram showing a pattern of fiducial markers located on an outer surface of a proximate object.

In an embodiment, if the proximate object 164 does not house an acoustic detector, it may house fiducial markers. FIG. 2 is a diagram showing a pattern of fiducial markers 208 located on an outer surface 200 of a proximate object 164. In an embodiment, the fiducial markers 208 are located on an outer surface 200 of the proximate object 164. In an embodiment, the proximate object 164 has fiducial markers 208 for backscattering the transmitted acoustic wave; the backscattered wavefronts from the fiducial markers 208 received by the acoustic receiver and are used to determine the position of the object. The fiducial markers 208 may create a strong acoustic backscatter, such as air-pockets of a known configuration.

In an embodiment, an outer surface 200 (e.g. of the proximate object 164) has fiducial markers 208 for absorbing light from the light source to produce an opto-acoustic wavefront; the acoustic wavefront 152 received by the acoustic receiver and are used to determine the position of the object. The fiducial markers 208 may create a strong opto-acoustic return signal. In an embodiment, the fiducial markers comprise carbon-black which is an optical absorber that produces strong signal upon illumination. In an embodiment, the fiducial markers 208 have an asymmetric pattern so that the orientation of the markers cannot be confused by an axis of symmetry.

In an embodiment, when a directed acoustic wave 162 is directed immediately towards a proximate object 164, this immediate direction will yield the highest intensity of the acoustic wave that reaches the proximate object 164; thus, upon receiving the highest intensity acoustic wave, the directional orientation becomes known. Furthermore, the propagation time, from when the wavefront originates until it is received, can also be clocked; combined with presumed or known the speed of sound in tissue, the distance between two proximate objects can be computed.

In an embodiment, the receiving elements of the acoustic receiver are in a linear array configuration; typically, would such elements be multiplexed as transmitting elements, the wavefront can be directed only in-plane, and not substantially out-of plane, thus it may be difficult to locate a proximate object 164 that is not directly in the imaging plane with such a configuration.

In an embodiment, fiducial markers are positioned in the direct path of the light source; thus, upon illumination by the light source, the fiducial markers become an acoustic source. In an embodiment, fiducial markers located on an optical window serving as an optical exit port to deliver optical energy to a volume. In an embodiment, due to the asymmetry of the marker pattern, the orientation and thus the identity of each marker is not confused. In an embodiment, the proximate object 164 is the acoustic receiver. The propagation time of each marker 208 in the marker pattern of the acoustic source can be measured by the acoustic receiver. By presuming or knowing the speed of sound in the tissue, the distance of each marker 208 to the acoustic receiver can be solved. Further, had a single marker been used, the position of the single marker 208 might be undetermined in 3D when using a linear array acoustic receiver which images a 2D imaging plane; when multiple markers are used, the orientation and position of the markers of known configuration can be fixed to a unique 3D position. Accordingly, in an embodiment, the position and orientation of the maker pattern in 3D is also solved. In an embodiment, this may be done by solving a least squares fit of the position and orientation against the received acoustic signals or against the computed distances. In an embodiment, a similar technique could be used in backscatter mode.

In an embodiment, the volume of tissue can be illuminated for opto-acoustic imaging while simultaneously producing the acoustic source for fiducial markers (this is a "passive mode"); in the event that the acoustic source signal interferes with an image in the imaging plane, any interfering signal from the fiducial marker's acoustic source can be subtracted or mitigated from the image. In an embodiment, the fiducial markers are powered by a light source separate from the main opto-acoustic imaging optical source, such as by single or multiple optical fibers illuminating the fiducials, which may operate separately (this is an "active mode"). In an embodiment, the fiducial acoustic source may be produced directly by acoustic transducers rather than by opto-acoustic waves generated by optical absorption. In an embodiment, an omni-directional acoustic wave may be produced from a coating the end of an illuminated optical fiber.

In an embodiment, opto-acoustic images may be enhanced by positioning an opto-acoustic light source at a first location to collect acoustic response and then at a second location to collect acoustic response; comparing the acoustic responses from first and second light source light; and then using at least a portion of information from first acoustic response location and second acoustic response location to produce an enhanced image. In an embodiment, the enhanced image mitigates the effects of optical fluence or optical penetration. In an embodiment, the image reveals contrast by displaying an image based on the difference between illumination at each location. In an embodiment, the fluence profile is solved, and mitigated from an absorption image.

Figure 3:
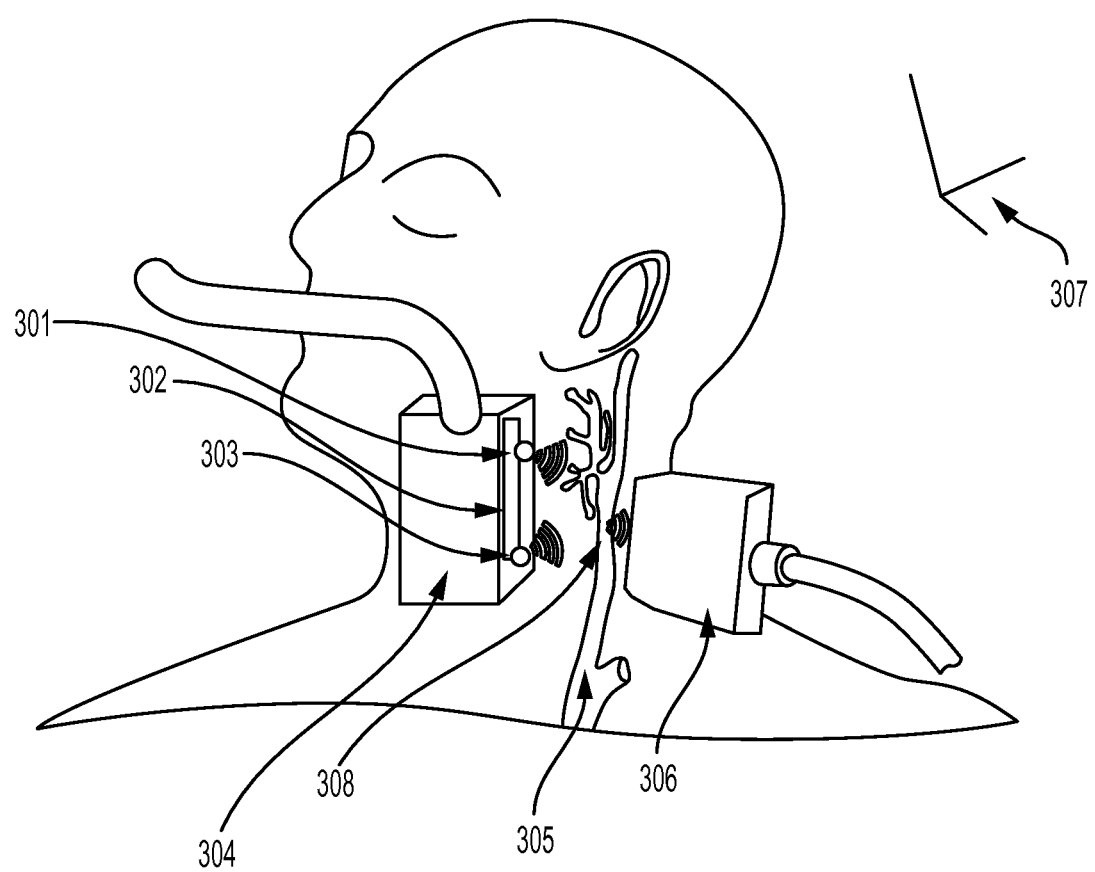
FIG. 3 is a perspective view showing an optical delivery unit with an optical energy exit port positioned to optically illuminate tissue of a subject, and an acoustic receiving unit positioned to receive opto-acoustic return signal from the illuminated tissue and acoustic signal from a fiducial marker site of the optical delivery unit.

FIG. 3 is a perspective view showing an optical delivery unit 304 with an optical energy exit port 302 positioned to optically illuminate tissue 305 of a subject, and an acoustic receiving unit 306 positioned to receive opto-acoustic return signal from an optically absorbing physiological structure 308 of the illuminated tissue 305 and acoustic signals from fiducial marker sites 301, 303 of the optical delivery unit 304. A coordinate reference frame is shown at 307.

In an embodiment, the invention can provide a method for determining position and orientation of an optical delivery unit 304 relative to an acoustic receiving unit 306, for applications in the field of opto-acoustic imaging. In an embodiment, the optical delivery unit 304 comprises a first fiducial marker site 301 configured to emit acoustic responses. In an embodiment, it comprises a second fiducial marker site 303 configured to emit acoustic responses. In an embodiment, the method comprises sampling and recording a plurality of acoustic signals from a volume of a subject. Each of the plurality of acoustic signals may be collected at a different data collection position relative to a coordinate reference frame 307. In an embodiment, the method comprises identifying in each of the plurality of acoustic signals a response of a first fiducial marker and, in an embodiment, a response of a second fiducial marker. Each identified response indicates a separation (e.g. a separation in time between clocked events or a separation in distance) between a fiducial marker site and a data collection position, where an acoustic signal is collected. In an embodiment, the separation is determined by determining the amount of time that has elapsed between a triggering event when an acoustic wave is initially emitted (e.g. by the fiducial marker site) until it is received by the acoustic receiver, and can be converted to distance by using a presumed speed of sound. The identified signal permits determining position and orientation of the optical delivery unit in the coordinate reference frame by using each of the identified responses of the first fiducial marker (and each of the identified responses of the second fiducial marker).

In certain circumstances, it is possible to determine position but not orientation using a single fiducial marker. In certain circumstances, using two or more fiducial markers permits determining relative position as well as relative orientation.

In an embodiment, the first fiducial marker and the second fiducial marker produce acoustic responses due to an absorption of optical energy that is delivered by the optical delivery unit. In an embodiment, a produced response of the first optically absorbing fiducial marker is stronger at a first predominant optical energy wavelength delivered by the optical delivery unit compared to that of a second predominant optical energy wavelength delivered by the optical delivery unit. In an embodiment, a produced response of the second fiducial marker is stronger at the second predominant optical energy wavelength compared to that of the first predominant optical energy wavelength. In an embodiment, the step of identifying for the responses comprises: locating a first target with a high intensity in a reconstructed sinogram for the first predominant optical energy wavelength and with a low intensity in a reconstructed sinogram for the second predominant optical energy wavelength; locating a second target with a low intensity in the reconstructed sinogram for the first predominant optical energy wavelength and with a high intensity in the reconstructed sinogram for the second predominant optical energy wavelength; identifying the response of the first fiducial marker as from the located first target; and, identifying the response of the second fiducial marker as from the located second target. Thus, in an embodiment, fiducial markers can be identified by having wavelength specific optical absorption.

In an embodiment, determining the position and orientation of the optical delivery unit comprises: determining values for a rotation matrix and a translation vector to rotate and translate vectors values that describe fiducial marker positions to a configuration (e.g. position and orientation) that fits to explain separations that are measured upon identifying the responses of the first fiducial marker and/or the identified responses of the second fiducial marker. In an embodiment, the separations are time separations measured in units of samples and are converted to distance separations by multiplying with a constant speed of sound for the volume and dividing with a constant sampling rate of an analog to digital converter. In an embodiment, the response of the first fiducial marker comprises a distinguishable acoustic response that can be distinguished from the response of the second fiducial marker. In an embodiment, each of the plurality of acoustic signals is processed. In an embodiment, an image of the volume using the processed acoustic signals is outputted to a display. In an embodiment, each identified response of the first fiducial marker comprises a distinguishable acoustic response, and the step of processing comprises separating distinguishable acoustic responses from each of the plurality of acoustic signals.

Methods for determining values for a rotation matrix and a translation vector to solve position and orientation in the context of wireless radio sensor networks is described by Equation 4b of Chepuri, Sundeep Prabhakar, et al. "Rigid Body Localization Using Sensor Networks." Signal Processing, IEEE Transactions on 62.18 (2014): 4911-4924, which is incorporated by reference herein.

In an embodiment, a system includes an optical energy delivery unit comprising optical energy exit port adapted to deliver optical energy to a volume of a subject; an acoustic receiving unit comprising acoustic receiver(s) adapted to receive acoustic signal from the volume; a fiducial marker site configured to emit acoustic response to be received by the acoustic receiving unit; a processing unit configured to perform processing of signals received by said acoustic receiving unit, which processing comprises determining a relative position of the optical energy delivery unit respective to the acoustic receiving unit using a received acoustic response emitted from the fiducial marker; and a display unit adapted to display an opto-acoustic image representing the volume. The opto-acoustic image may produced by using information about the determined relative position, because such information may help to enhance the resulting opto-acoustic image (e.g. fluence compensation, light source correction, etc.). In an embodiment, an additional fiducial marker site is configured to emit acoustic responses to be received by said acoustic receiver. In an embodiment, the processing unit determines a relative orientation and/or the relative position of the optical energy delivery unit respective to the acoustic receiving unit using a received acoustic response emitted by the fiducial marker site and/or a received acoustic response emitted by additional fiducial marker site. In an embodiment, the fiducial marker site and the additional fiducial marker site are located on a distal surface of the optical energy delivery unit. In an embodiment, the optical energy exit port is located on the distal surface of the optical energy delivery unit. In an embodiment, the processing performed by the processing unit further comprises the steps of: i) retrieving a list of position values respective to a first coordinate reference frame (typically the list would comprise a position for the fiducial marker site and a position for the additional fiducial marker site); ii) determining values for a rotation matrix and a translation vector to rotate and translate the list of position values to a configuration respective to a second coordinate reference frame (typically, the determined values would comprise a solution that accounts for propagation delays of fiducial response component of the signals received by the acoustic receiving unit); and, iii) producing the relative orientation and the relative position per the rotation matrix and translation vector, which can then be used.

In an embodiment, the processing unit is further configured to perform steps comprising: i) separating a distinguishable acoustic response component emitted by the fiducial marker from remaining components of the signals received by the acoustic receiving unit; and, ii) generating an opto-acoustic image of the volume using those remaining components. The generation of opto-acoustic images using separated components is further described in U.S. patent application Ser. No. 14/512,896 entitled "Systems And Methods For Component Separation In Medical Imaging," which is incorporated herein by reference. Such techniques may be used to separate the signal of the fiducial marker from the remainder of the opto-acoustic signal to improve generated images when using fiducial markers.

In an embodiment, the processing unit is further configured to perform steps comprising: i) generating a first opto-acoustic representation of the volume when the optical energy delivery unit is at a first relative placement respective to a placement of the acoustic receiving unit as determined by the processing unit; ii) generating a second opto-acoustic representation of the volume when the optical energy delivery unit is at a second relative placement respective to the placement of said acoustic receiving unit as determined by said processing unit; iii) computing a difference between the first opto-acoustic representation of the volume and the second opto-acoustic representation of the volume; and iv) generating an image to display based on the computed difference. In an embodiment, the generated image is an image spatially representing the computed difference. The differences that occur within the volume between two or more different optical illumination conditions may yield useful insight about the physical details of the volume.

In an embodiment, the processing unit is configured to perform steps comprising: determining when the optical energy delivery unit and acoustic receiving unit are suitably located at relative position with respect to one another to form a proper opto-acoustic image. For example, in certain circumstances, if the optical energy delivery unit is too far away, the optical energy may be too weak and result in a poor image, so detecting when this does or does not occurs is of benefit. Furthermore, using systems and methods described herein, it is possible to determine when both of the optical energy unit and acoustic receiving unit are acoustically coupled to the volume, which could signify proper placement of the units. For example, if the optical delivery unit is not touching the volume, this may prevent an acoustic signal from a fiducial marker from reaching the acoustic receiver, and thus could be used to determine if the unit is in contact with the volume, which is useful if making contact with the volume is required for proper illumination, or in an embodiment, if loss of contact with the volume triggers a safety mechanism to prevent delivery of optical energy.

In an embodiment, a system includes an acoustic receiver located on a distal surface of a primary contact unit. The primary contact unit makes contact with the volume. In an embodiment, the primary contact unit comprises a distal end that includes its distal surface. In an embodiment, the distal end of the primary contact unit is adapted to acoustically couple with a surface of a volume (e.g. of tissue). In an embodiment, the primary contact unit further comprises a proximal end, that is positioned away from the distal end. In an embodiment, a first optically absorbing fiducial is located on a distal surface of a secondary contact unit. The secondary contact unit also makes contact with the volume. In an embodiment, the secondary contact unit comprises a distal end that includes its distal surface. In an embodiment, the distal end of the secondary contact unit is adapted to acoustically couple with the volume. In an embodiment, the system comprises a processing subsystem configured to perform processing comprising: i) identifying responses of the first optically absorbing fiducial (and/or of the second optically absorbing fiducial) by analyzing signals received by the acoustic receiver; and, ii) determining the position and orientation of the secondary contact unit respective to the primary contact unit using the identified responses.

Figure 4:
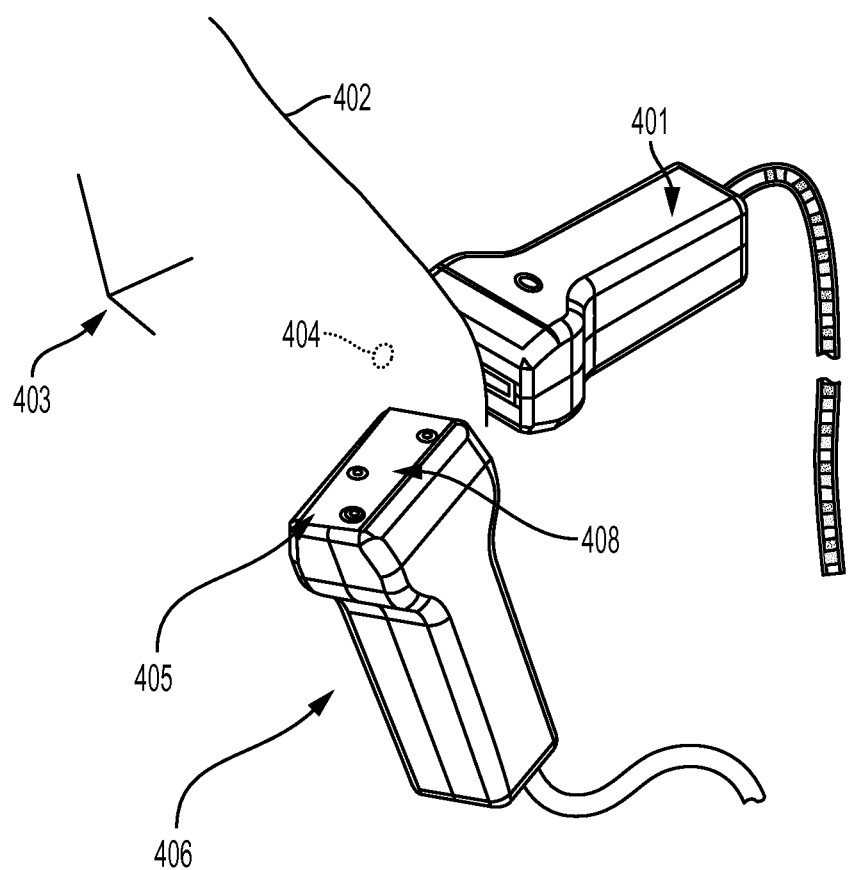
FIG. 4 is a perspective view showing optical energy being delivered to tissue at a position in a coordinate reference frame relative to a second position where acoustic signal is received from the tissue.

FIG. 4 is a perspective view showing optical energy being delivered by optical delivery unit 406 to an object of interest 404 within the tissue being imaged, the optical delivery unit being located at a first position in a coordinate reference frame 403 relative to a second position where acoustic signal is received from the tissue. Fiducial markers 408 are provided on the optical exit port/optical window 405 of the optical delivery unit 406.

Figure 5:
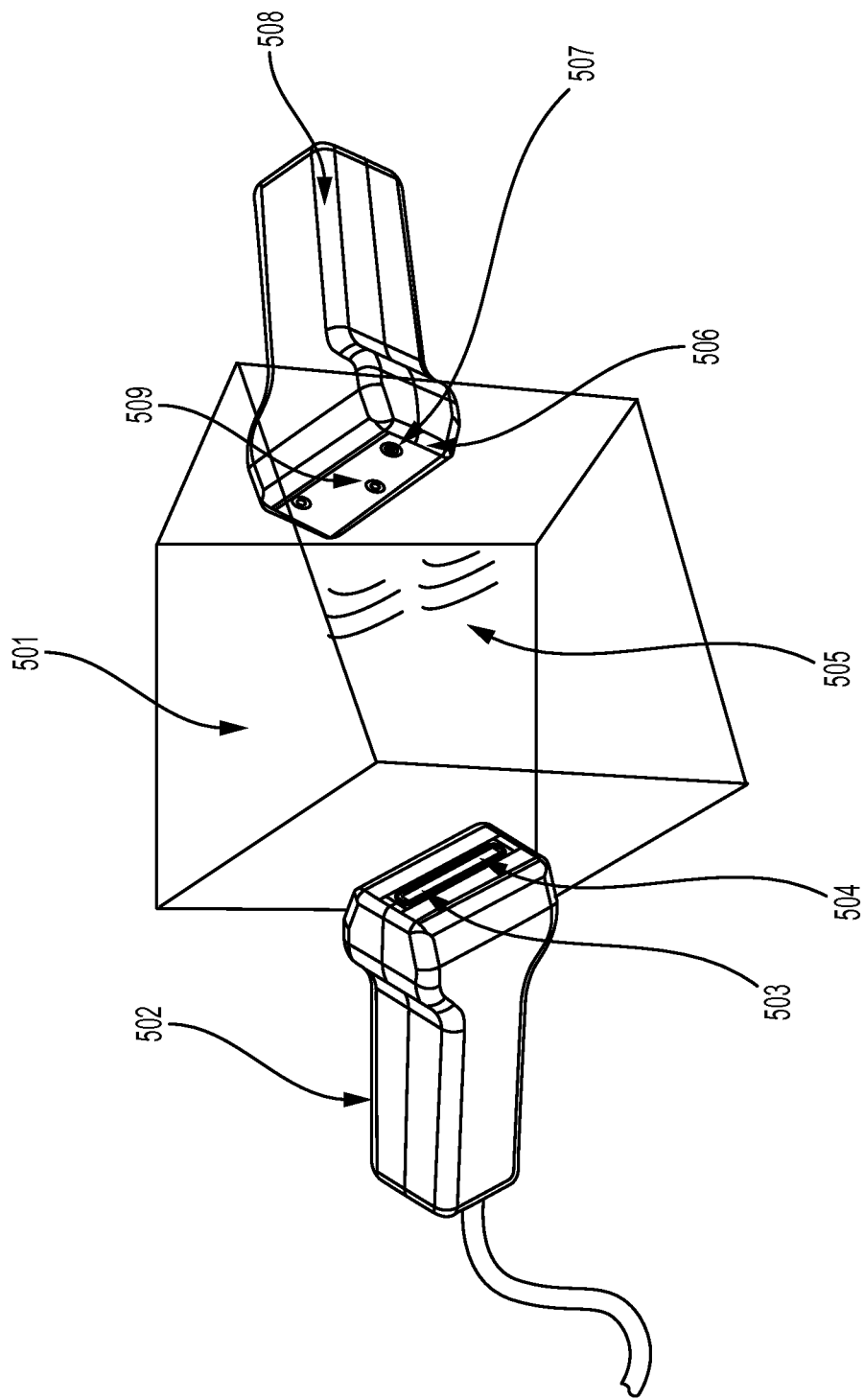
FIG. 5 is a perspective view showing a primary contact unit comprising a plurality of acoustic receivers at data collection positions in contact with a volume, and a secondary contact unit comprising an optically absorbing fiducial marking forming a pattern which emits an acoustic response that propagates through the volume.

In an embodiment, the first optically absorbing fiducial comprises a first optically absorbing pattern which when activated by an optical energy produces an acoustic response that can be received by the acoustic receiver. FIG. 5 is a perspective view showing a primary contact unit 502 comprising a plurality of acoustic receivers at first and second data collection positions 503, 504 in contact with a volume 501, and a secondary contact unit 508 comprising an optically absorbing fiducial marking 509 at a distal surface 506, the fiducial marking 509 forming a pattern 507 which emits an acoustic response 505 that propagates through the volume 501. In typical use, the primary contact unit 502 and the secondary contact unit 508 are both coupled to the volume 501. In FIG. 5, the primary contact unit 502 is shown decoupled from the volume 501 for illustrative purposes only.

In an embodiment, the fiducial comprises radially symmetric spherical layers. In an embodiment, the fiducial contains optically absorbing concentric rings. In an embodiment, a second optically absorbing fiducial is located on the distal surface of the secondary contact unit, and the second optically absorbing fiducial comprises a second optically absorbing pattern. In an embodiment, the first optically absorbing pattern comprises an optically absorbing material with a greater optical absorption coefficient at a predominant wavelength of the optical energy compared to an optical absorption coefficient of the distal surface for the same predominant wavelength. In an embodiment, the optically absorbing material is selected from the group consisting of: a toner, a dye, a colorant, a screen printing ink, a plastisol based ink, a PVC based ink, a chemical deposit, a masked screening deposit, an adhesive film, and a decal. In an embodiment, the produced acoustic response of the fiducial comprises a distinguishable acoustic response component, which is characterized by a unique frequency spectral characteristic corresponding to the first optically absorbing pattern. In an embodiment, an emitter comprising concentric spherical layers, or concentric rings on a flat surface, may be used to produce unique frequency spectral characteristic, which is adjustably by varying the geometry and intensity of the layers or rings.

Figure 6:
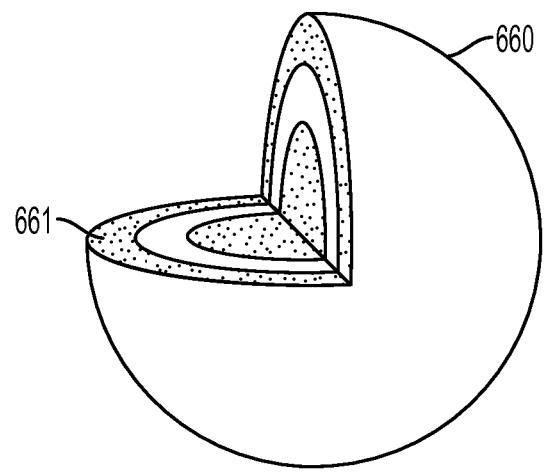
FIG. 6 is a diagram showing an optically absorbing radially symmetric emitter.

With reference to FIG. 6, in an embodiment, an emitter to multi-directionally emit acoustic signals with approximately equal signal content towards all relevant directions is based on such a physical phenomenon which occurs in radially symmetric opto-acoustic sources. In an embodiment, a radially symmetric emitter 660 comprises a first concentric layer 661 comprising a carrier material and a first concentration of an electromagnetically absorbing material; and, a second concentric layer comprising the carrier material and a second concentration of the electromagnetically absorbing material; wherein the emitter is adapted to emit, following the absorption of electromagnetic energy, an acoustic signal toward a first heading and a similar signal toward a second heading, which acoustic signal emitted toward the first heading is essentially the same as the similar signal emitted toward the second heading, in a manner whereby an acoustic receiver configured to detect signal from the emitter will receive the same signal regardless of if it is positioned to receiving the signal by way of the first heading or positioned elsewhere to receive the signal by way of the second heading. In an embodiment, the emitter further comprises additional concentric layers, wherein each additional concentric layer comprises the carrier material and a concentration of the electromagnetically absorbing material. Such an emitter is shown in FIG. 6. In an embodiment, the outermost diameter of the emitter is 1 mm, thus the emitter may serve as a compact fiducial on the surface of a handheld unit in contact with a volume of tissue. In an embodiment, such an emitter may scale to larger (or smaller) sizes suitable for a variety of applications where emitting similar and/or identifiable acoustic signals to multiple positions is desired.

In an embodiment, the concentric layers are spherical. In an embodiment, the emitter emits an omni-directional acoustic response corresponding to a radically symmetric energy absorption profile. In an embodiment, the concentration of the electromagnetically absorbing material is smoothly varied between successive concentric layers to achieve a continuous band-limited emitted acoustic signal profile. The time domain signal received at time t at a distance x away from a radially symmetric profile is $p(t-t0, x)=(x-c*(t-t0))/x*H(|x-c*(t-t0)|)$, where $H(|x|)$ is a function describing the radial profile, c is the speed of sound, and t0 is the time of the emission. In an embodiment, the radial profile of a physical object $G(|x|)$ that will provide a heating profile $H(|x|)$ is dependent on the fluence of the optical energy reaching portions of the physical object. This makes it possible to control and predict the received signal by constructing an appropriate radial source. The time domain shape is $H(|x-c*(t-t0)|)$, thus in an embodiment, is possible to identify different fiducial markers by detecting different such time domain shapes. In an embodiment, the emitted acoustic signal comprises an identifiable acoustic signal due to unique concentration of electromagnetically absorbing material in each layer, wherein the identifiable acoustic signal can be identified by processing when the emitted acoustic signal is received by an acoustic receiver. In an embodiment, identifying the signal involves correlating a (processed) received signal with a known unique signature of a fiducial, and determining if and where the correlation is greatest (or greater than a threshold). In an embodiment, the correlation is cross-correlation performed in the frequency domain and converted back to the time domain to determine cross-correlation peaks. In an embodiment, the unique concentration of electromagnetically absorbing material in each layer generates a binary code representing the digits zero and one based on either a first or a second concentration of electromagnetically absorbing material. In an embodiment, this is used to create a unique signature. In an embodiment, the different unique signatures corresponding to different identifiable fiducial are orthogonal, so one fiducial would be less likely to be confused with another. In an embodiment, the unique concentration of electromagnetically absorbing material in each layer generates a unique time domain or frequency domain signature. In an embodiment, the electromagnetically absorbing material is optically absorbing material. In an embodiment, the carrier material is a polymer such as a plastisol and the optically absorbing material is a colorant. In an embodiment, the layers of the spherical emitter are manufactured by suspending a spherical core object by a wire and dipping in a series of material baths comprising carrier and varied concentration of absorber to form layer. In an embodiment, the layers are manufactured by vapor deposition process, where the optical absorption of each layer is controlled by varying the optical absorption of each layer. In an embodiment, a light source or optical fibre is at the center of the spherical core. In an embodiment the emitter is a bead. In an embodiment, the emitter is embedded in the outer surface of a handheld probe. In embodiment, the emitter is a buoy. In an embodiment, the emitter is a spherical tip affixed to the end of an optical fibre.

Figure 7A:
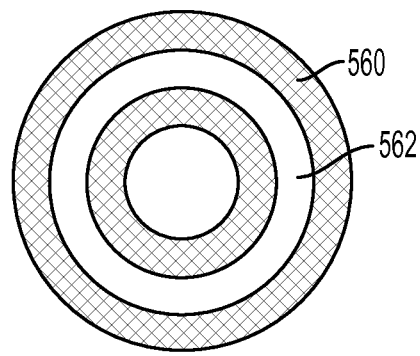
FIGS. 7a and 7b are diagrams showing an optically absorbing fiducial marker pattern with concentric rings.
Figure 7B:
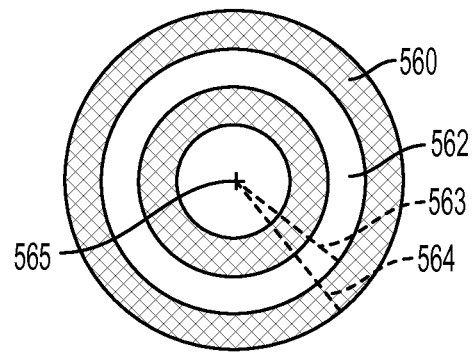

With reference to FIGS. 7a and 7b, in an embodiment, a fiducial is a decal shaped like an archer's target that is printed on a surface 562 to be coupled to a volume. The geometry (i.e., sizes and spacing of rings) of the archer's target shape can be varied to influence the resulting optoacoustic signal. In an embodiment, an optically absorbing fiducial marker adapted to emit an identifiable acoustic signal, comprising: a surface 562 (e.g. an outer surface of an optical delivery unit adapted to couple with a volume) comprising a first material and a second material, the first material having an optical absorption coefficient that is greater than that of the second material, wherein the first material is patterned on the surface 562 to form a plurality of optically absorbing concentric rings 560, which concentric rings 560 are concentric to a common point 565 on the surface 562, each concentric ring 560 having an inner radius 563 and an outer radius 564 dimension, and for each ring 560 the first material is distributed on the surface 562 spanning from a radial distance of its inner radius 563 to its outer radius 564 with respect to the common point 565. In an embodiment, each of the plurality of optically absorbing concentric rings 560 comprises a thin layer of the first material adhered to the second material. In an embodiment, the bulk of the surface is made from the second material. In an embodiment, the second material is a plastic, and the first material is an ink. In an embodiment, the surface 562 is adapted to emit an identifiable acoustic signal resulting from the absorption of optical energy by the concentric rings 560, the identifiable acoustic signal encoding the spatial distribution of the concentric rings 560 to permit identification of the fiducial marker by processing of signal received by an acoustic receiver. In an embodiment, the surface 562 further comprises a set of additional optically absorbing concentric rings, which additional concentric rings are concentric to a second point on the surface that is different from the common point. For example, the surface can have two identifiable markers on it.

In an embodiment, a fiducial comprises optically reflective material which has weaker optical absorption (e.g. than a material it is adhered to), and a pattern which produces acoustic signal due to strong optical absorption is associated with a relief portion of the pattern that does not comprise the optically reflective material.

Some aspects of the system and method disclosed above can be embodied, at least in part, in software. That is, the techniques may be carried out in a special purpose or general purpose computer system or other data processing system in response to its processor, such as a microprocessor, executing sequences of instructions contained in a memory, such as ROM, volatile RAM, non-volatile memory, cache or a remote storage device. Functions expressed in the claims may be performed by a processor in combination with memory storing code and should not be interpreted as means-plus-function limitations.

Routines executed to implement the embodiments may be implemented as part of an operating system, firmware, ROM, middleware, service delivery platform, SDK (Software Development Kit) component, web services, or other specific application, component, program, object, module or sequence of instructions referred to as "computer programs." Invocation interfaces to these routines can be exposed to a software development community as an API (Application Programming Interface). The computer programs typically comprise one or more instructions set at various times in various memory and storage devices in a computer, and that, when read and executed by one or more processors in a computer, cause the computer to perform operations necessary to execute elements involving the various aspects.

A machine-readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer-to-peer networks. Different portions of the data and instructions can be obtained from different centralized servers and/or peer-to-peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine-readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others.

In general, a machine readable medium includes any mechanism that provides (e.g., stores) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

The above embodiments and preferences are illustrative of the present invention. It is neither necessary, nor intended for this patent to outline or define every possible combination or embodiment. The inventor has disclosed sufficient information to permit one skilled in the art to practice at least one embodiment of the invention. The above description and drawings are merely illustrative of the present invention and that changes in components, structure and procedure are possible without departing from the scope of the present invention as defined in the following claims. For example, elements and/or steps described above and/or in the following claims in a particular order may be practiced in a different order without departing from the invention. Thus, while the invention has been particularly shown and described with reference to embodiments thereof, it will be understood by those skilled in the art that various changes in form and details may be made therein without departing from the spirit and scope of the invention.

What is claimed is:

1. A method for determining position and orientation of an optical delivery unit relative to an acoustic receiving unit, the method comprising:

sampling and recording acoustic signals from a volume of a subject, the acoustic signals collected by the acoustic receiving unit;

identifying an acoustic response of a first fiducial marker and an acoustic response of a second fiducial marker based on the acoustic signals, wherein the acoustic responses indicate time separations between times of emission of the acoustic signals from a corresponding one of first and second fiducial marker sites and times of reception of the acoustic signals by the acoustic receiving unit at a data collection position relative to a coordinate reference frame; and, determining position and orientation of the optical delivery unit in the coordinate reference frame based on the acoustic response of the first fiducial marker and the acoustic response of the second fiducial marker.

2. The method of claim 1, wherein the acoustic responses of the first fiducial marker and the second fiducial marker are based on an absorption of optical energy by the first fiducial marker and the second fiducial marker that is delivered by the optical delivery unit.

3. The method of claim 2, wherein the acoustic response of the first fiducial marker is stronger at a first predominant optical energy wavelength delivered by the optical delivery unit compared to that of a second predominant optical energy wavelength delivered by the optical delivery unit.

4. The method of claim 3, wherein the acoustic response of the second fiducial marker is stronger at the second predominant optical energy wavelength compared to that of the first predominant optical energy wavelength.

5. The method of claim 4, wherein the step of identifying the acoustic response of the first fiducial marker and the acoustic response of the second fiducial marker comprises:

locating a first target with a relatively high intensity in a reconstructed sinogram for the first predominant optical energy wavelength and with a relatively low intensity in a reconstructed sinogram for the second predominant optical energy wavelength;

locating a second target with a second relatively low intensity in the reconstructed sinogram for the first predominant optical energy wavelength and with a second relatively high intensity in the reconstructed sinogram for the second predominant optical energy wavelength;

identifying the acoustic response of the first fiducial marker as from the located first target; and, identifying the acoustic response of the second fiducial marker as from the located second target.

6. The method of claim 1, wherein determining the position and orientation of the optical delivery unit comprises:

determining values for a rotation matrix and a translation vector to rotate and translate values for fiducial marker positions to a configuration that fits to explain time separations that are measured upon identifying the acoustic response of the first fiducial marker and the acoustic response of the second fiducial marker.

7. The method of claim 6, wherein the time separations are measured in units of samples and are converted to distance separations by multiplying with a constant speed of sound for the volume and dividing with a constant sampling rate of an analog to digital converter.

8. The method of claim 1, wherein the acoustic response of the first fiducial marker can be distinguished from the acoustic response of the second fiducial marker.

9. The method of claim 1, wherein the method further comprises the steps of:

processing the acoustic signals to produce processed acoustic signals; and, outputting to a display an image of the volume using the processed acoustic signals.

10. The method of claim 9, wherein the acoustic response of the first fiducial marker comprises a distinguishable acoustic response, and the step of processing comprises:

separating the distinguishable acoustic response from another acoustic response of the acoustic signals.

11. A system comprising:

an optical energy delivery unit comprising an optical energy exit port adapted to deliver optical energy to a volume of a subject;

an acoustic receiving unit configured to receive acoustic signals from the volume;

first and second fiducial marker sites configured to emit acoustic response to be received by the acoustic receiving unit;

a processing unit configured to perform processing of the acoustic signals received by the acoustic receiving unit, including determining a relative position of the optical energy delivery unit respective to the acoustic receiving unit;

wherein determining the relative position of the optical energy delivery unit respective to the acoustic receiving unit includes determining a time separation between a first time corresponding to emission of an acoustic signal of the acoustic signals from a corresponding one of the first and second fiducial marker sites and a second time when at least a portion of the acoustic signal is received at the acoustic receiving unit; and, display unit adapted to display an opto-acoustic image representing the volume.

12. The system of claim 11, wherein the opto-acoustic image is produced, at least in part, by using data describing the determined relative position.

13. The system of claim 11, further comprising:

wherein the processing by the processing unit further comprises determining a relative orientation and the relative position of said optical energy delivery unit respective to the acoustic receiving unit using a received acoustic response emitted of the first fiducial marker site and a received acoustic response emitted of the second fiducial marker site.

14. The system of claim 13, wherein the first fiducial marker site and the second fiducial marker site are located on a distal surface of said optical energy delivery unit.

15. The system of claim 14, wherein the optical energy exit port is located on the distal surface of said optical energy delivery unit.

16. The system of claim 13, wherein the processing performed by the processing unit further comprises the steps of:

retrieving a list of position values relative to a first coordinate reference frame, the list comprising a position for the first fiducial marker site and a position for the second fiducial marker site;

determining values for a rotation matrix and a translation vector to rotate and translate the list of position values to a configuration relative to a second coordinate reference frame, wherein the determined values comprise a solution that accounts for propagation delays of fiducial response component of the acoustic signals received by said acoustic receiving unit; and, producing the relative orientation and the relative position per the rotation matrix and translation vector.

17. The system of claim 11, wherein the processing unit is further configured to perform steps comprising:

separating a distinguishable acoustic response component emitted by said fiducial marker from remaining components of the acoustic signals received by the acoustic receiving unit; and, generating an opto-acoustic image of the volume using said remaining components.

18. The system of claim 11, wherein the processing unit is further configured to perform steps comprising:

generating a first opto-acoustic representation of the volume when said optical energy delivery unit is at a first relative placement respective to a placement of the acoustic receiving unit as determined by said processing unit;

generating a second opto-acoustic representation of the volume when said optical energy delivery unit is at a second relative placement respective to the placement of the acoustic receiving unit as determined by said processing unit;

computing a difference between the first opto-acoustic representation of the volume and the second opto-acoustic representation of the volume; and generating an image to display said computed difference.

19. The system of claim 11, wherein the processing unit is further configured to determine when the optical energy delivery unit and acoustic receiving unit are within a proximity adequate to form an opto-acoustic image.

20. A system, comprising:

an acoustic receiver located on a distal surface of a primary contact unit, the primary contact unit comprising a distal end including its distal surface, the distal end of the primary contact unit being adapted to acoustically couple with a surface of a volume of tissue, the primary contact unit further comprising a proximal end;

a first optically absorbing fiducial located on a distal surface of a secondary contact unit, the secondary contact unit comprising a distal end including its distal surface, which distal end of the secondary contact unit is adapted to acoustically couple with the volume; and, a processing subsystem configured to perform processing comprising:

identifying acoustic responses of the first optically absorbing fiducial and of the second optically absorbing fiducial by analyzing acoustic signals received by the acoustic receiver; and, determining the position of the secondary contact unit respective to the primary contact unit using the identified responses;

wherein the acoustic responses are based on time separations between an acoustic wave emitted at a fiducial marker site and receiving the acoustic wave emitted at a data collection position.

21. The system of claim 20, wherein the first optically absorbing fiducial comprises a first optically absorbing pattern which when activated by an optical energy produces an acoustic response that can be received by the acoustic receiver.

22. The system of claim 21, further comprising, a second optically absorbing fiducial located on the distal surface of the secondary contact unit, wherein the second optically absorbing fiducial comprises a second optically absorbing pattern.

23. The system of claim 21, wherein the first optically absorbing pattern comprises an optically absorbing material with a greater optical absorption coefficient at a predominant wavelength of the optical energy compared to an optical absorption coefficient of the distal surface for the same predominant wavelength.

24. The system of claim 23, wherein the optically absorbing material is selected from the group consisting of: a toner, a dye, a colorant, a screen printing ink, a plastisol based ink, a PVC based ink, a chemical deposit, a masked screening deposit, an adhesive film, and a decal.

25. The system of claim 21, wherein the produced acoustic response comprises a distinguishable acoustic response component, which distinguishable acoustic response component is characterized by a unique frequency spectral characteristic corresponding to the first optically absorbing pattern.

* * * * *